United States Patent
Fujiyama et al.

(10) Patent No.: US 12,195,709 B2
(45) Date of Patent: Jan. 14, 2025

(54) CO-CULTURE APPARATUS, CO-CULTURE SYSTEM, AND CO-CULTURE METHOD

(71) Applicants: SHIMADZU CORPORATION, Kyoto (JP); TOKYO INSTITUTE OF TECHNOLOGY, Tokyo (JP)

(72) Inventors: Yoichi Fujiyama, Kyoto (JP); Yoh-ichi Tagawa, Tokyo (JP)

(73) Assignees: SHIMADZU CORPORATION, Kyoto (JP); TOKYO INSTITUTE OF TECHNOLOGY, Tokyo (JP)

( * ) Notice: Subject to any disclaimer, the term of this patent is extended or adjusted under 35 U.S.C. 154(b) by 87 days.

(21) Appl. No.: 17/679,247

(22) Filed: Feb. 24, 2022

(65) Prior Publication Data

US 2022/0267705 A1    Aug. 25, 2022

(30) Foreign Application Priority Data

Feb. 25, 2021  (JP) ................................ 2021-028695
Jan. 21, 2022  (JP) ................................ 2022-007634

(51) Int. Cl.
*C12M 1/00*   (2006.01)
*C12M 1/12*   (2006.01)
*C12M 1/42*   (2006.01)

(52) U.S. Cl.
CPC ............ *C12M 23/34* (2013.01); *C12M 25/04* (2013.01); *C12M 29/04* (2013.01); *C12M 35/08* (2013.01)

(58) Field of Classification Search
CPC ...... C12M 23/34; C12M 25/04; C12M 29/04; C12M 35/08; C12M 25/02; C12M 41/00; C12M 41/32; C12M 23/02; C12M 25/10
See application file for complete search history.

(56) References Cited

U.S. PATENT DOCUMENTS

| | | | |
|---|---|---|---|
| 2009/0281370 A1* | 11/2009 | Lindenberg .......... | C12N 5/0609 600/35 |
| 2015/0072413 A1 | 3/2015 | Zenhausern et al. | |
| 2019/0382703 A1 | 12/2019 | Katayama et al. | |
| 2021/0079356 A1* | 3/2021 | Novak .................... | C12N 1/20 |

FOREIGN PATENT DOCUMENTS

| | | | | |
|---|---|---|---|---|
| JP | 2017-136082 A | | 8/2017 | |
| WO | WO-2012118799 A2 | * | 9/2012 | ............ C12M 21/08 |
| WO | 2018/079793 A1 | | 5/2018 | |

OTHER PUBLICATIONS

Bonakdar, M., Graybill, P. M., & Davalos, R. V. (2017). A microfluidic model of the blood-brain barrier to study permeabilization by pulsed electric fields. RSC advances, 7(68), 42811-42818. (Year: 2017).*
Japanese Office Action dated Dec. 20, 2022 in Japanese Application No. 2022-007634.
Sasan Jalili-Firoozinezhad et al., "A complex human gut microbiome cultured in an anaerobic intestine-on-a-chip", Nat. Biomed. Eng., 2019, vol. 3, No. 7, pp. 520-531, with Supplementary information, pp. 1-16 (50 pgs total).
Japanese Office Action dated Apr. 18, 2023 in Japanese Application No. 2022-007634.

* cited by examiner

*Primary Examiner* — Christopher M Babic
*Assistant Examiner* — Masudur Rahman
(74) *Attorney, Agent, or Firm* — Sughrue Mion, PLLC

(57) ABSTRACT

A co-culture apparatus includes: a first airtight container; a co-culture device disposed outside of the first airtight container; a first culture medium source disposed in the first airtight container and storing a first culture medium; a second culture medium source storing a second culture medium having a lower dissolved oxygen concentration than that of the first culture medium; and a first conduit connected to the co-culture device and the first culture medium source. The co-culture device includes: a membrane having a first main surface, and a second main surface opposite to the first main surface for culturing cells; a first flow path partially defined by the first main surface and disposed such that the first culture medium flows therethrough; and a second flow path partially defined by the second main surface and disposed such that the second culture medium flows therethrough. The first flow path has an inlet connected to the first conduit.

8 Claims, 7 Drawing Sheets

CO-CULTURE APPARATUS, CO-CULTURE SYSTEM, AND CO-CULTURE METHOD

BACKGROUND OF THE INVENTION

Field of the Invention

The present invention relates to a co-culture apparatus, a co-culture system, and a co-culture method.

Description of the Background Art

Development of a device that simulates the intestinal environment and the like has been promoted for the purpose of studying drug kinetics, drug metabolism and the like. PTL 1 (WO 2018/079793) discloses a system that simulates the intestinal environment by disposing, in an anaerobic chamber, a device having intestinal epithelial cells seeded on a porous membrane.

SUMMARY OF THE INVENTION

In conventional techniques including PTL 1, it is difficult to evaluate over time both a culture medium flowing in an anaerobic environment and a culture medium flowing in an aerobic environment.

The present invention provides a co-culture apparatus, a co-culture system, and a co-culture method capable of evaluating over time both a culture medium flowing in an anaerobic environment and a culture medium flowing in an aerobic environment.

A co-culture apparatus according to the first aspect of the present invention includes: a first airtight container; a co-culture device disposed outside of the first airtight container; a first culture medium source disposed in the first airtight container and storing a first culture medium; a second culture medium source storing a second culture medium having a lower dissolved oxygen concentration than that of the first culture medium; and a first conduit connected to the co-culture device and the first culture medium source. The co-culture device includes: a membrane having a first main surface, and a second main surface opposite to the first main surface, the second main surface configured for culturing cells; a first flow path partially defined by the first main surface, the first flow path disposed such that the first culture medium flows therethrough; and a second flow path partially defined by the second main surface, the second flow path disposed such that the second culture medium flows therethrough. The first flow path has an inlet connected to the first conduit.

A co-culture system according to the second aspect of the present invention includes: an anaerobic chamber; and the above-described co-culture apparatus disposed in the anaerobic chamber.

A co-culture method according to the third aspect of the present invention includes: placing a co-culture apparatus in an anaerobic chamber, the co-culture apparatus including a membrane having a first main surface, and a second main surface opposite to the first main surface for culturing cells, a first flow path partially defined by the first main surface, and a second flow path partially defined by the second main surface; supplying a first culture medium to the first flow path; and supplying a second culture medium to the second flow path, the second culture medium having a lower dissolved oxygen concentration than that of the first culture medium. The first culture medium supplied to the first flow path is maintained in an aerobic environment within the anaerobic chamber.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
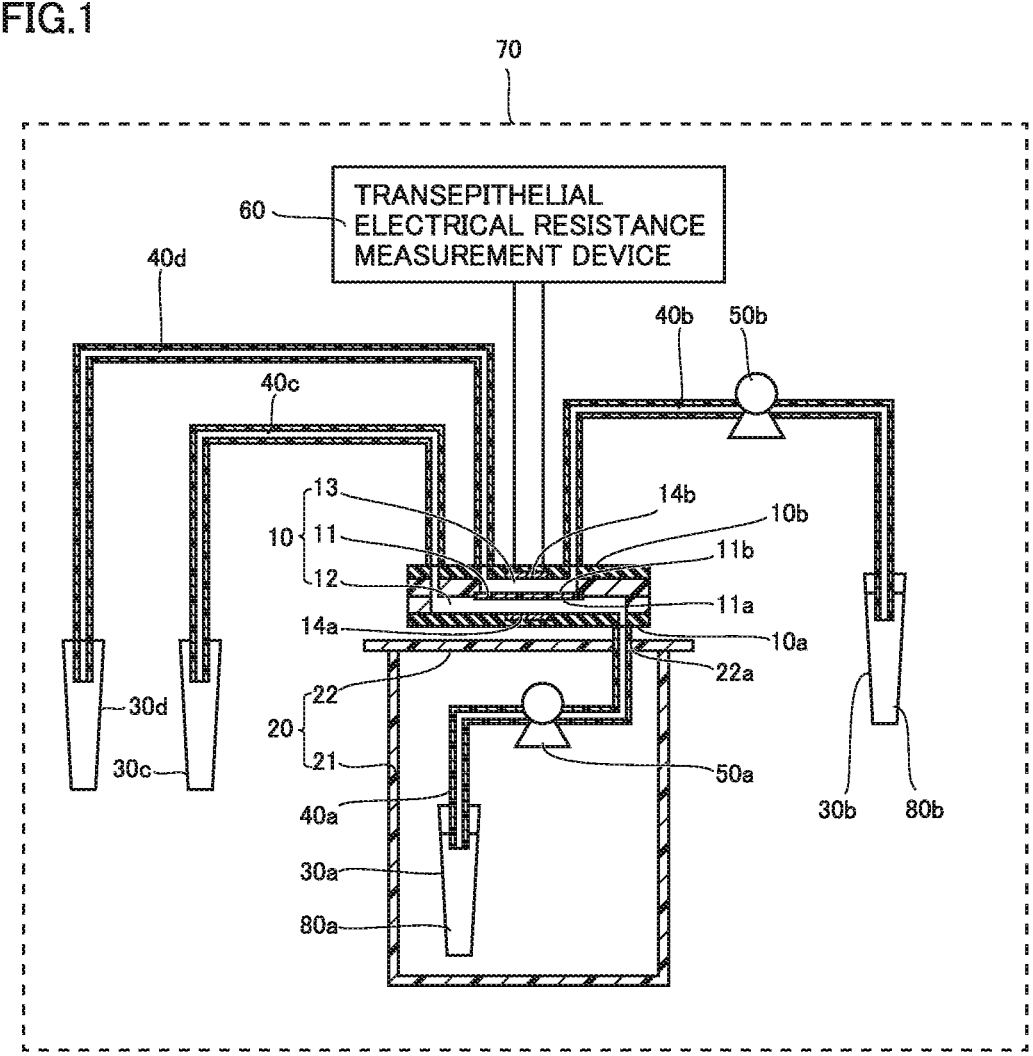
FIG. 1 is a schematic cross-sectional view of a co-culture system according to an embodiment.

Embodiments will be described in detail with reference to the drawings. The same or corresponding parts are designated by the same reference characters in the drawings below, and redundant description will not be repeated.

Co-Culture System According to Embodiment

A co-culture system according to an embodiment is described below.

Schematic Configuration of Co-Culture System According to Embodiment

FIG. 1 is a schematic cross-sectional view of the co-culture system according to the embodiment. As shown in FIG. 1, the co-culture system according to the embodiment includes a co-culture device 10 and a first airtight container 20. The co-culture system according to the embodiment includes a first culture medium container 30a, a second culture medium container 30b, a third culture medium container 30c, and a fourth culture medium container 30d. The co-culture system according to the embodiment includes a first tube 40a, a second tube 40b, a third tube 40c, and a fourth tube 40d.

The co-culture system according to the embodiment includes a first pump 50a, a second pump 50b, and a transepithelial electrical resistance measurement device 60.

Co-culture device 10 has a first surface 10a and a second surface 10b. First surface 10a faces first airtight container 20. Second surface 10b is opposite to first surface 10a. Co-culture device 10 includes therein a membrane 11, a first flow path 12, and a second flow path 13. Co-culture device 10 is disposed outside of first airtight container 20.

Membrane 11 has a first main surface 11a and a second main surface 11b. Second main surface 11b is opposite to first main surface 11a. Second main surface 11b is a surface of membrane 11 for culturing cells. The cells cultured on second main surface 11b are, for example, intestinal epithelial cells that form tight junctions on second main surface 11b. A specific example of the cells cultured on second main surface 11b is Caco-2 cells.

Membrane 11 is, for example, a track-etched membrane made of polycarbonate. Membrane 11 may be, for example, a porous membrane made of PET (polyethylene terephthalate) or other materials, or a collagen vitrigel membrane. Membrane 11 is not particularly limited so long as cell culture is possible on second main surface 11b, and oxygen and nutrients can be supplied from first main surface 11a.

First flow path 12 is partially defined by first main surface 11a. Second flow path 13 is partially defined by second main surface 11b. First flow path 12 is a flow path through which a first culture medium 80a flows, and second flow path 13 is a flow path through which a second culture medium 80b flows.

Second culture medium 80b has a lower dissolved oxygen concentration than that of first culture medium 80a. In other words, first culture medium 80a is an aerobic culture medium and second culture medium 80b is an anaerobic culture medium. Second culture medium 80b may contain bacteria. The bacteria contained in second culture medium 80b are anaerobic bacteria, for example.

During the flow of first culture medium 80a through first flow path 12, oxygen in first culture medium 80a is supplied through membrane 11 to the cells being cultured on second main surface 11b. Thus, even if the dissolved oxygen concentration in second culture medium 80b is low, the cells being cultured on second main surface 11b can be maintained.

First airtight container 20 is a container whose interior space can be sealed in an air-tight manner. The interior space of first airtight container 20 is maintained in an aerobic environment. More specifically, the interior space of first airtight container 20 is maintained in an atmospheric environment. First airtight container 20 includes a body 21 and a lid 22. Body 21 is tubular. Body 21 has a lower end closed by a bottom wall, and has an open upper end. Lid 22 is removably attached to the upper end of body 21. A through hole 22a extending through lid 22 in the thickness direction is formed in lid 22. A non-contact oxygen monitor (for example, a spot sensor capable of measuring the amount of oxygen by applying excitation light) may be disposed in first airtight container 20. The amount of residual oxygen in first airtight container 20 can thereby be checked.

First culture medium 80 is stored in first culture medium container 30a. First culture medium container 30a and an inlet of first flow path 12 are connected by first tube 40a. First tube 40a is disposed in first airtight container 20. First tube 40a connects first culture medium container 30a and the inlet of first flow path 12 through through hole 22a.

Second culture medium 80b is stored in second culture medium container 30b. Second culture medium container 30b and an inlet of second flow path 13 are connected by second tube 40b. Second tube 40b is disposed outside of first airtight container 20. The inlet of first flow path 12 is at first surface 10a. The inlet of second flow path 13 is at second surface 10b.

Third culture medium container 30c and an outlet of first flow path 12 are connected by third tube 40c. Fourth culture medium container 30d and an outlet of second flow path 13 are connected by fourth tube 40d. Third tube 40c and fourth tube 40d are disposed outside of first airtight container 20. The outlet of first flow path 12 is at second surface 10b. The outlet of second flow path 13 is at second surface 10b.

First pump 50a supplies first culture medium 80a stored in first culture medium container 30a to first flow path 12 via first tube 40a. First pump 50a supplies first culture medium 80a discharged from first flow path 12 to third culture medium container 30c via third tube 40c. First pump 50a is attached to first tube 40a. In other words, first pump 50a is disposed in first airtight container 20. However, first pump 50a may be disposed outside of first airtight container 20 (may be attached to third tube 40c).

Second pump 50b supplies second culture medium 80b stored in second culture medium container 30b to second flow path 13 via second tube 40b. Second pump 50b supplies second culture medium 80b discharged from first flow path 12 to fourth culture medium container 30d via fourth tube 40d. Second pump 50b is attached to second tube 40b. In other words, second pump 50b is disposed outside of first airtight container 20. However, second pump 50b may be attached to fourth tube 40d.

First tube 40a, second tube 40b, third tube 40c, and fourth tube 40d are, for example, tubes made of PTFE (polytetrafluoroethylene), PEEK (polyether ether ketone), silicone, and the like. First pump 50a is a roller pump, for example. Second pump 50b is a roller pump, for example.

Co-culture device 10 includes a first electrode 14a and a second electrode 14b. Transepithelial electrical resistance measurement device 60 is electrically connected to first electrode 14a and second electrode 14b. Transepithelial electrical resistance measurement device 60 thereby measures an electrical resistance value between first culture medium 80a flowing through first flow path 12 and second culture medium 80b flowing through second flow path 13.

This electrical resistance value increases when the cells being cultured on second main surface 11b form tight junctions, and decreases when the cells being cultured on second main surface 11b do not form tight junctions. By measuring this electrical resistance value with transepithelial electrical resistance measurement device 60, therefore, the state of the cells being cultured on second main surface 11b can be monitored.

An anaerobic environment is maintained within an anaerobic chamber 70. A co-culture apparatus according to the embodiment is disposed in anaerobic chamber 70.

Detailed Configuration of Co-Culture Device 10

Figure 2:
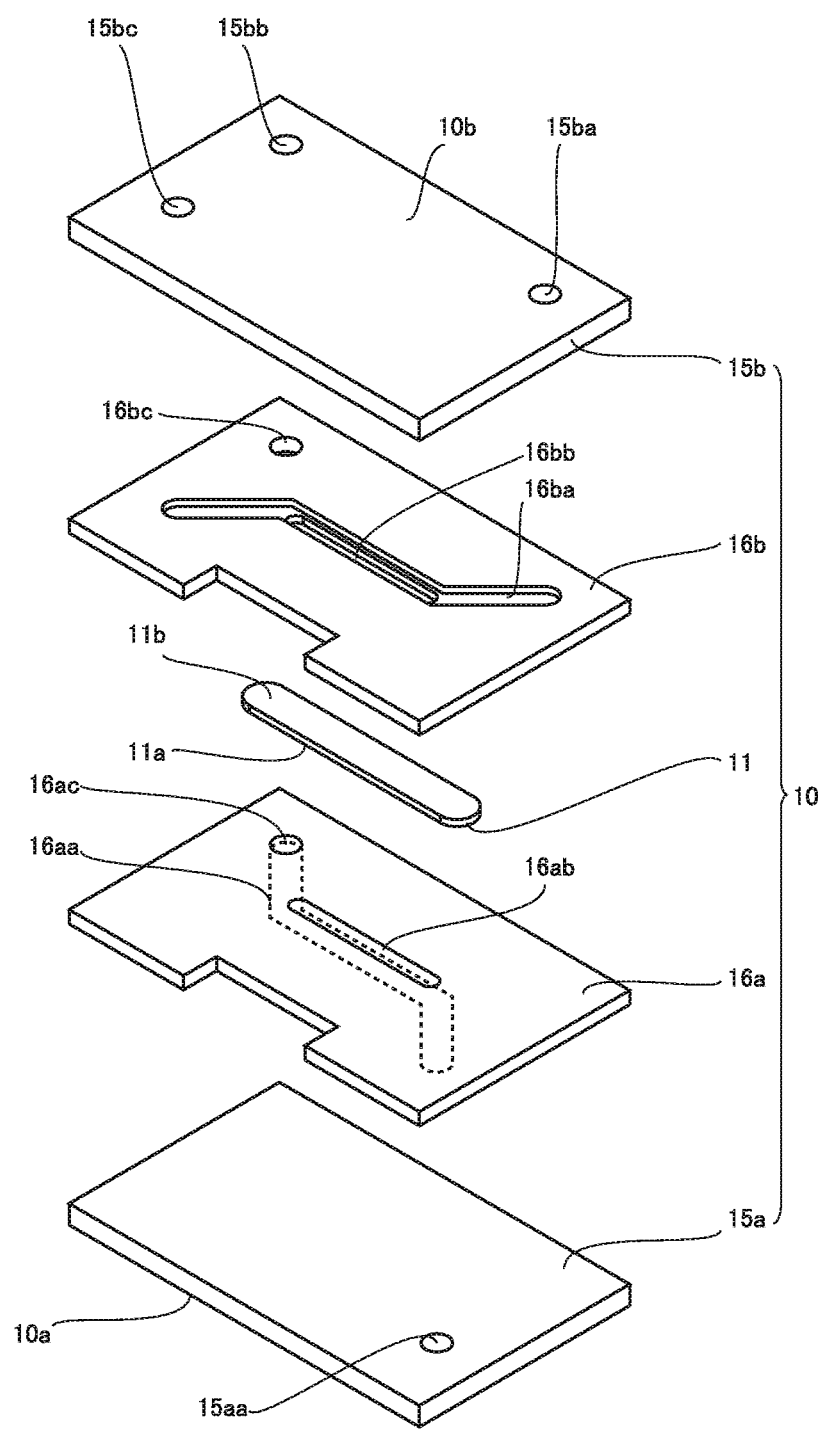
FIG. 2 is an exploded perspective view of a co-culture device 10.

FIG. 2 is an exploded perspective view of co-culture device 10. As shown in FIG. 2, co-culture device 10 has a structure in which membrane 11, a first glass plate 15a, a second glass plate 15b, a first sheet 16a, and a second sheet 16b are stacked. First sheet 16a and second sheet 16b are made of a resin material, for example. A specific example of this resin material is silicone rubber.

First glass plate 15a is disposed on the first surface 10a side. A through hole 15aa is formed in first glass plate 15a. Through hole 15aa extends through first glass plate 15a in the thickness direction. Through hole 15aa serves as the inlet of first flow path 12.

Second glass plate 15b is disposed on the second surface 10b side. A through hole 15ba, a through hole 15bb, and a through hole 15bc are formed in second glass plate 15b. Through hole 15ba serves as the inlet of second flow path 13. Through hole 15bb serves as the outlet of first flow path 12. Through hole 15bc serves as the outlet of second flow path 13.

Membrane 11 is sandwiched between first sheet 16a and second sheet 16b. First main surface 11a of membrane 11 faces first sheet 16a, and second main surface 11b of membrane 11 faces second sheet 16b. First sheet 16a and second sheet 16b are in contact with each other except for the portion where membrane 11 is sandwiched between them.

First sheet 16a and second sheet 16b are sandwiched between first glass plate 15a and second glass plate 15b. First sheet 16a is in contact with first glass plate 15a. Second sheet 16b is in contact with second glass plate 15b.

Although not shown, first electrode 14a is formed on a surface of first glass plate 15a facing first sheet 16a, and second electrode 14b is formed on a surface of second glass plate 15b facing second sheet 16b. First electrode 14a and second electrode 14b are made of platinum, for example. First electrode 14a and second electrode 14b are formed by sputtering, for example.

A groove 16aa is formed in a surface of first sheet 16a facing first glass plate 15a. Groove 16aa is located to overlap through hole 15aa. A through hole 16ab and a through hole 16ac are formed in first sheet 16a. Through hole 16ab and through hole 16ac extend through first sheet 16a in the thickness direction. Through hole 16ab and through hole 16ac are located to overlap groove 16aa.

A groove 16ba is formed in a surface of second sheet 16b facing second glass plate 15b. Groove 16ba is located to overlap through hole 15ba and through hole 15bc.

A through hole 16bb and a through hole 16bc are formed in second sheet 16b. Through hole 16bb and through hole 16bc extend through second sheet 16b in the thickness direction. Through hole 16bb is located to overlap groove 16ba. Through hole 16bb is located to overlap through hole 16ab. Through hole 16ab and through hole 16bb are closed by membrane 11. Through hole 16bc is located to overlap through hole 15bb and through hole 16ac.

Through hole 15aa, groove 16aa, through hole 16ac, through hole 16bc, through hole 15bb, and first main surface 11a of membrane 11 form first flow path 12. Through hole 15ba, groove 16ba, through hole 15bc, and second main surface 11b of membrane 11 form second flow path 13.

The bonding of first glass plate 15a and first sheet 16a, the bonding of first sheet 16a and second sheet 16b, and the bonding of second sheet 16b and second glass plate 15b are performed, for example, by applying pressure to bonded surfaces while the bonded surfaces are activated with oxygen plasma.

Figure 3:
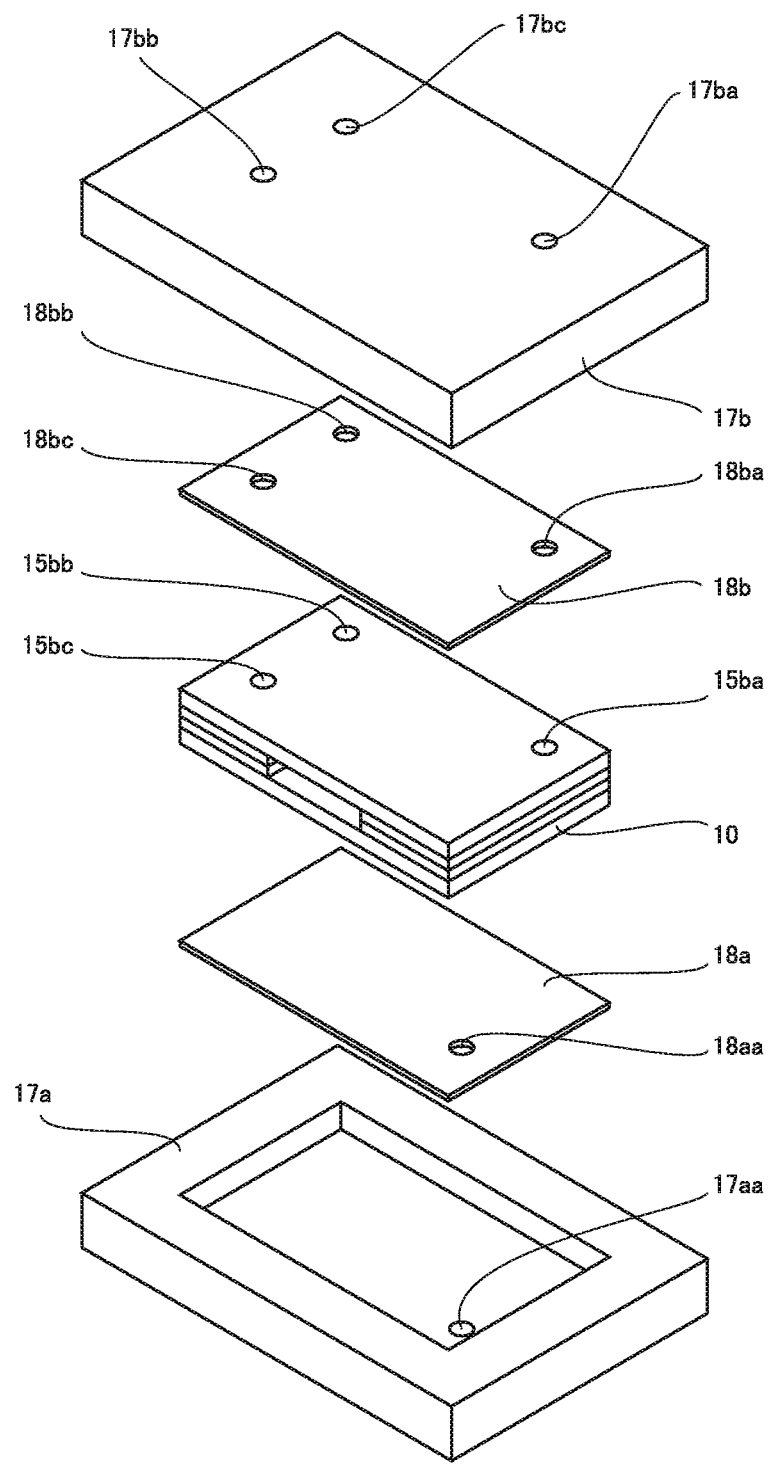
FIG. 3 is an exploded perspective view illustrating how to attach a first holder 17a and a second holder 17b to co-culture device 10.

FIG. 3 is an exploded perspective view illustrating how to attach a first holder 17a and a second holder 17b to co-culture device 10. As shown in FIG. 3, co-culture device 10 is sandwiched between first holder 17a and second holder 17b. A first rubber sheet 18a is sandwiched between first holder 17a and co-culture device 10. A second rubber sheet 18b is sandwiched between second holder 17b and co-culture device 10.

First holder 17a and second holder 17b are made of polyether ether ketone resin (PEEK resin), for example. First rubber sheet 18a and second rubber sheet 18b are made of butyl rubber, for example.

A through hole 17aa is formed in first holder 17a. Through hole 17aa extends through first holder 17a in the thickness direction. Through hole 17aa overlaps through hole 15aa when first holder 17a is attached to co-culture device 10. A through hole 18aa is formed in first rubber sheet 18a. Through hole 18aa overlaps through hole 15aa when first holder 17a is attached to co-culture device 10. In other words, first tube 40a passing through through hole 22a is connected to through hole 15aa (the inlet of first flow path 12) through through hole 17aa and through hole 18aa.

A through hole 17ba, a through hole 17bb, and a through hole 17bc are formed in second holder 17b. Through hole 17ba, through hole 17bb, and through hole 17bc extend through second holder 17b in the thickness direction. A through hole 18ba, a through hole 18bb, and a through hole 18bc are formed in second rubber sheet 18b. Through hole 18ba, through hole 18bb, and through hole 18bc extend through second rubber sheet 18b in the thickness direction.

Through hole 17ba, through hole 17bb, and through hole 17bc overlap through hole 15ba, through hole 15bb, and through hole 15bc, respectively, when second holder 17b is attached to co-culture device 10. Through hole 18ba, through hole 18bb, and through hole 18bc overlap through hole 15ba, through hole 15bb, and through hole 15bc, respectively, when second holder 17b is attached to co-culture device 10. Second tube 40b is connected to through hole 15ba (the inlet of second flow path 13) through through hole 17ba and through hole 18ba. Third tube 40c is connected to through hole 15bb (the outlet of first flow path 12) through through hole 17bb and through hole 18bb. Fourth tube 40d is connected to through hole 15bc (the outlet of second flow path 13) through through hole 17bc and through hole 18bc.

Co-culture device 10 is attached to lid 22 of first airtight container 20 in the state of being sandwiched between first holder 17a and second holder 17b. This attaching is performed by screwing, for example.

Co-Culture Method According to Embodiment

A co-culture method according to the embodiment is described below.

Figure 4:
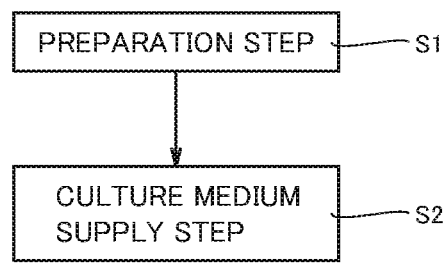
FIG. 4 is a flowchart of a co-culture method according to the embodiment.

FIG. 4 is a flowchart of the co-culture method according to the embodiment. As shown in FIG. 4, the co-culture method according to the embodiment includes a preparation step S1 and a culture medium supply step S2. Culture medium supply step S2 is performed after preparation step S1.

In preparation step S1, the co-culture apparatus according to the embodiment is placed in anaerobic chamber 70. In culture medium supply step S2, first culture medium 80a stored in first culture medium container 30a is supplied to first flow path 12 via first tube 40a. Additionally, in culture medium supply step S2, second culture medium 80b stored in second culture medium container 30b is supplied to second flow path 13 via second tube 40b. The supply of first culture medium 80a to first flow path 12 is performed by driving first pump 50a. The supply of second culture medium 80b to second flow path 13 is performed by driving second pump 50b. As a result, co-culture of cells and bacteria is performed in co-culture device 10.

By driving first pump 50a, first culture medium 80a that has flowed through first flow path 12 is supplied to third culture medium container 30c via third tube 40c. By driving second pump 50b, second culture medium 80b that has flowed through second flow path 13 is supplied to fourth culture medium container 30d via fourth tube 40d. First culture medium 80a stored in third culture medium container 30c and second culture medium 80b stored in fourth culture medium container 30d are subjected to mass spectrometry using, for example, a liquid chromatography mass spectrometry method.

Effects of Co-Culture System According to Embodiment

Effects of the co-culture system according to the embodiment are described below as compared to a comparative example.

Figure 5:
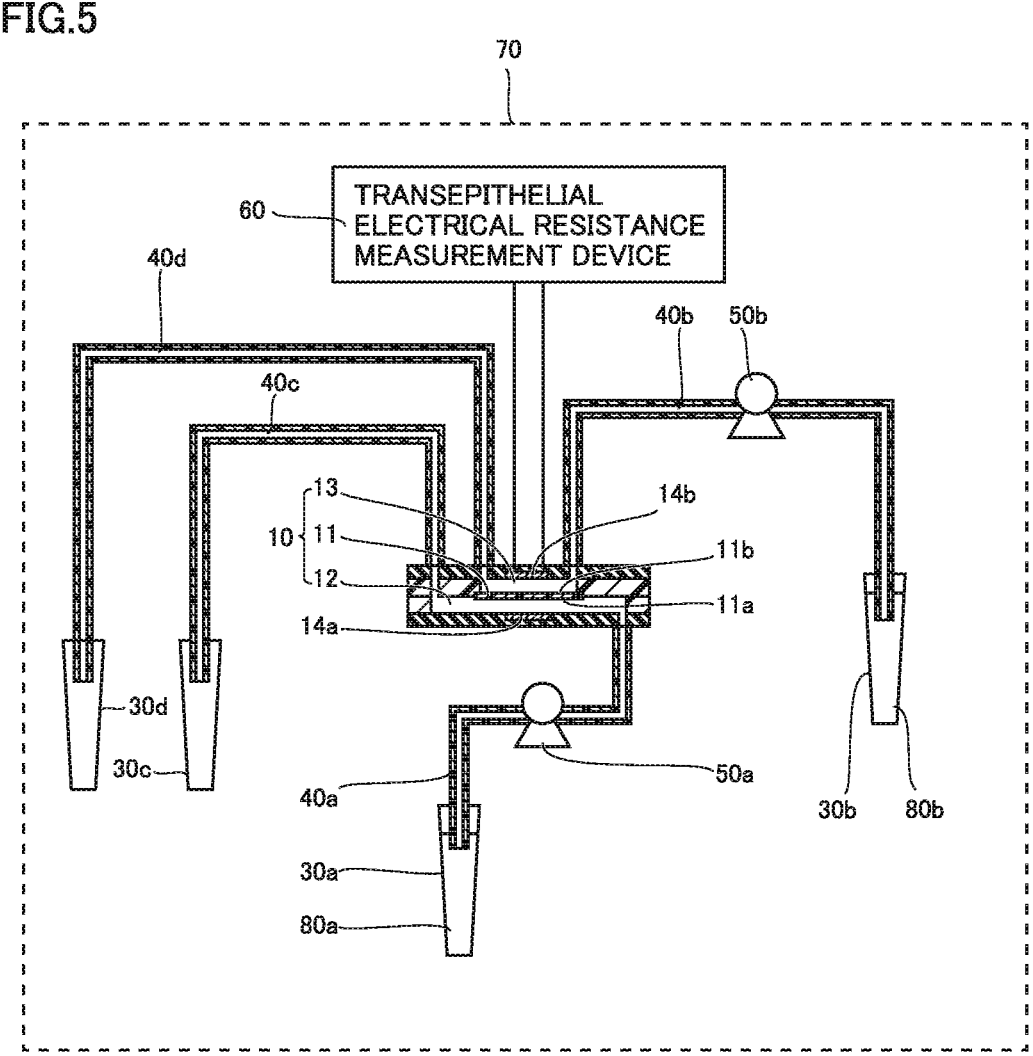
FIG. 5 is a schematic cross-sectional view of a co-culture system according to a comparative example.

FIG. 5 is a schematic cross-sectional view of a co-culture system according to the comparative example. The co-culture system according to the comparative example does not include first airtight container 20, as shown in FIG. 5. The co-culture system according to the comparative example is otherwise identical to the co-culture system according to the embodiment.

In the co-culture system according to the comparative example, since first culture medium container 30a and first tube 40a are not disposed in first airtight container 20, first culture medium 80a stored in first culture medium container 30a and supplied to first flow path 12 is exposed to the anaerobic environment in anaerobic chamber 70. In the co-culture system according to the embodiment, on the other hand, since first culture medium container 30a and first tube 40a are disposed in first airtight container 20, first culture medium 80a stored in first culture medium container 30a is supplied to first flow path 12 without being exposed to the anaerobic environment.

Additionally, in the co-culture system according to the embodiment, since second culture medium container 30b and second tube 40b are disposed in anaerobic chamber 70, second culture medium 80b stored in second culture medium container 30b flows under the anaerobic environment and is supplied to second flow path 13. In this manner, according to the co-culture system in the embodiment, it is possible to evaluate over time both a culture medium flowing in an aerobic environment (first culture medium 80a) and a culture medium flowing in an anaerobic environment (second culture medium 80b).

In the co-culture system according to the embodiment, since the outlet of first flow path 12 (through hole 15bb), the inlet of second flow path 13 (through hole 15ba), and the outlet of second flow path 13 (through hole 15bc) are formed in second surface 10b, while the inlet of first flow path 12 (through hole 15aa) is formed in first surface 10a facing first airtight container 20, the inlet of first flow path 12 and first culture medium container 30a can be readily connected by first tube 40a, with first culture medium container 30a disposed in first airtight container 20.

Co-Culture System According to First Modification

A co-culture system according to a first modification is described below. The difference from the co-culture system according to the embodiment will mainly be described here, and redundant description will not be repeated.

Figure 6:
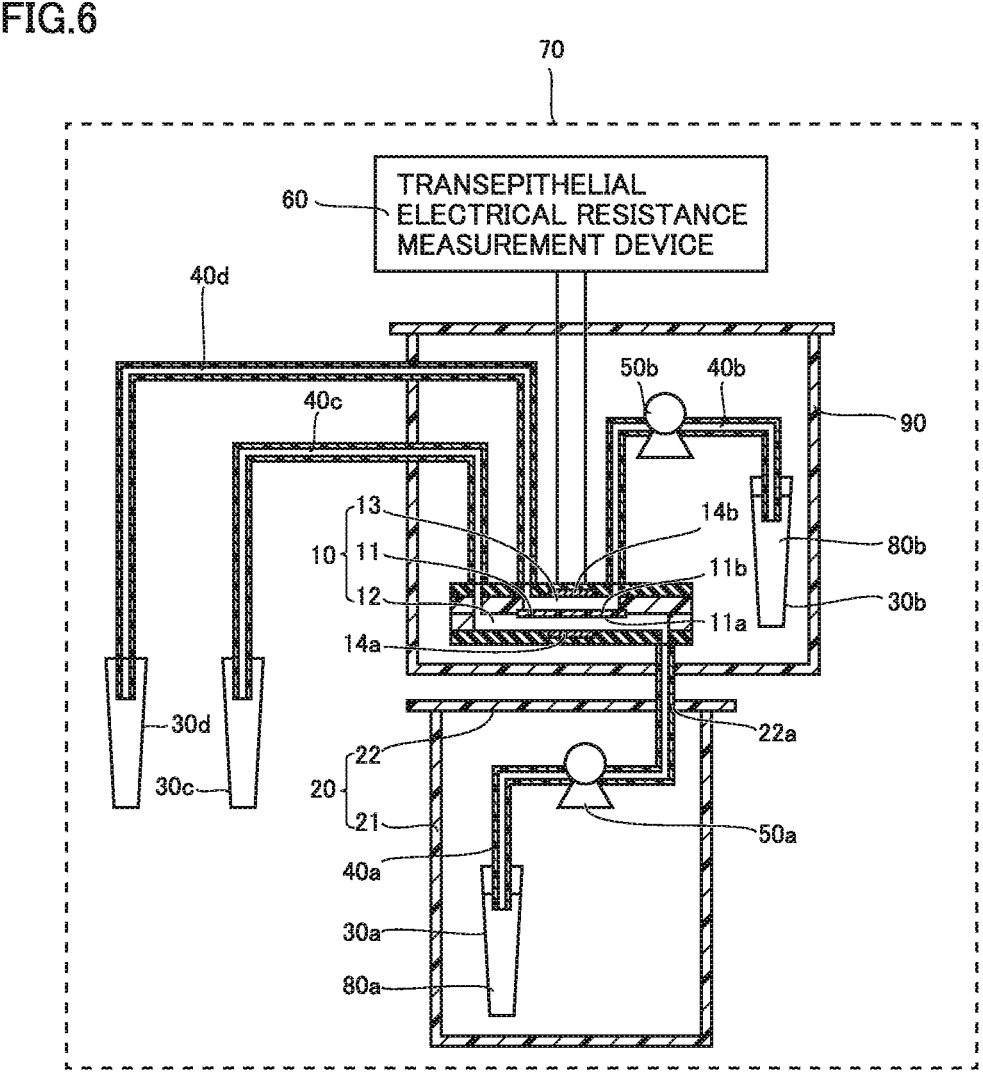
FIG. 6 is a schematic cross-sectional view of a co-culture system according to a first modification.

FIG. 6 is a schematic cross-sectional view of the co-culture system according to the first modification. The culture system according to the first modification includes a second airtight container 90, as shown in FIG. 6. Second airtight container 90 has an interior space that is sealed in an air-tight manner. Co-culture device 10, second pump 50b, and second culture medium container 30b are disposed in second airtight container 90. The co-culture system according to the first modification is otherwise identical to the co-culture system according to the embodiment. Second pump 50b and second culture medium container 30b may be disposed outside of second airtight container 90.

If the evaluation is to be conducted over a long period of time (for example, several days), first airtight container 20 may need to be taken out of anaerobic chamber 70 in order to replace first culture medium 80a stored in first culture medium container 30a. In this case, the anaerobic environment in co-culture device 10 cannot be maintained.

In the co-culture system according to the first modification, since co-culture device 10, second pump 50b, and second culture medium container 30b are disposed in second airtight container 90, even if the oxygen concentration in anaerobic chamber 70 temporarily increases when first airtight container 20 is taken out of anaerobic chamber 70 in order to replace first culture medium 80a stored in first culture medium container 30a, it is possible to maintain co-culture device 10, second pump 50b, and second culture medium container 30b in the anaerobic environment.

Co-Culture System According to Second Modification

A co-culture system according to a second modification is described below. The difference from the co-culture system according to the embodiment will mainly be described here, and redundant description will not be repeated.

Figure 7:
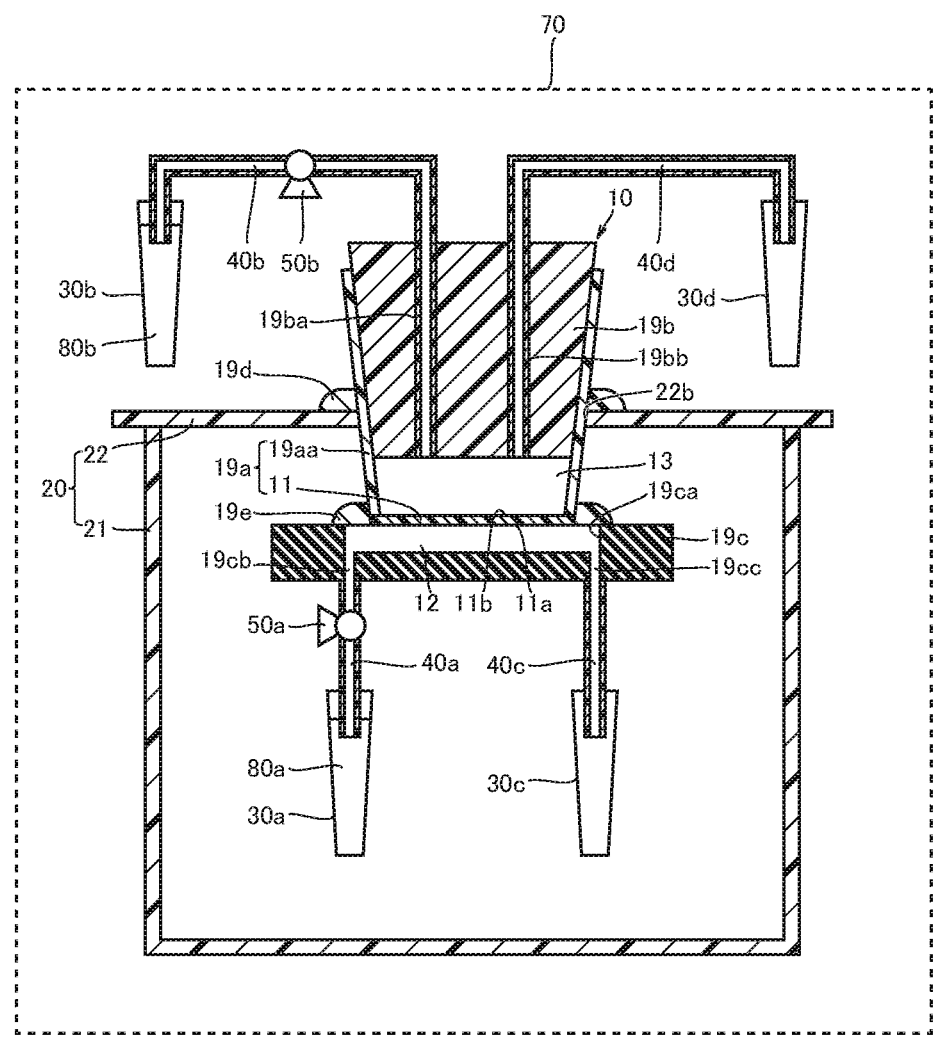
FIG. 7 is a schematic cross-sectional view of a co-culture system according to a second modification.

FIG. 7 is a schematic cross-sectional view of the co-culture system according to the second modification. In the co-culture system according to the second modification, as shown in FIG. 7, co-culture device 10 includes a culture tank 19a, an adapter 19b, and a flow path plate 19c, instead of the stacked structure of co-culture device 10 in the co-culture system according to the embodiment.

Culture tank 19a is a cell culture insert, for example. Culture tank 19a includes a tubular portion 19aa and membrane 11. Tubular portion 19aa is made of a resin material, for example. Membrane 11 closes the lower end side of tubular portion 19aa. First main surface 11a and second main surface 11b face the outer side and the inner side of culture tank 19a (tubular portion 19aa), respectively.

A through hole 22b is formed in lid 22, which extends through lid 22 in the thickness direction and communicates with the inside of first airtight container 20. The lower end side of culture tank 19a is inserted into through hole 22b so as to be located in first airtight container 20. The space between culture tank 19a and through hole 22b is sealed with a gas sealing portion 19d. The airtightness in first airtight container 20 is thereby maintained. Gas sealing portion 19d is an O-ring, for example.

Adapter 19b is inserted into tubular portion 19aa from the upper end side so as to be spaced from membrane 11 (second main surface 11b). A space defined by the bottom surface of adapter 19b, the inner wall surface of tubular portion 19aa, and second main surface 11b forms second flow path 13. Adapter 19b is made of rubber, for example.

A through hole 19ba and a through hole 19bb are formed in adapter 19b. Through hole 19ba and through hole 19bb extend through adapter 19b in a direction from the upper surface of adapter 19b toward the bottom surface of adapter 19b. Through hole 19ba and through hole 19bb communicate with second flow path 13. Second tube 40b and fourth tube 40d are inserted into through hole 19ba and through hole 19bb, respectively. Second tube 40b and fourth tube 40d are thereby connected to second flow path 13.

Flow path plate 19c is a plate-shaped member. Flow path plate 19c is disposed in first airtight container 20. A groove 19ca, a through hole 19cb, and a through hole 19cc are formed in flow path plate 19c. Groove 19ca is formed in one main surface of flow path plate 19c. The one main surface of flow path plate 19c faces culture tank 19a. Through hole 19cb and through hole 19cc are formed in the other main surface of flow path plate 19c so as to extend through flow path plate 19c in the thickness direction and communicate with groove 19ca.

Culture tank 19a is disposed on flow path plate 19c so that first main surface 11a faces groove 19ca. The space between culture tank 19a and groove 19ca is sealed in a liquid-tight manner by a liquid sealing portion 19e. Liquid sealing portion 19e is, for example, a seal or an O-ring made of PDMS (polydimethylsiloxane). Groove 19ca, through hole 19cb, through hole 19cc, liquid sealing portion 19e, and first main surface 11a form first flow path 12. First tube 40a and third tube 40c are connected to through hole 19cb and through hole 19cc, respectively. The co-culture system according to the second modification is otherwise identical in configuration to the co-culture system according to the embodiment.

In the co-culture system according to the second modification, since first culture medium container 30a and first tube 40a are disposed in first airtight container 20, first culture medium 80a stored in first culture medium container 30a is supplied to first flow path 12 without being exposed to the anaerobic environment. Additionally, in the co-culture system according to the second modification, since second culture medium container 30b and second tube 40b are disposed in anaerobic chamber 70, second culture medium 80b stored in second culture medium container 30b flows under the anaerobic environment and is supplied to second flow path 13. In this manner, according to the co-culture system in the second modification as well, it is possible to evaluate over time both a culture medium flowing in an aerobic environment (first culture medium 80a) and a culture medium flowing in an anaerobic environment (second culture medium 80b).

Though embodiments of the present invention have been described, it should be understood that the embodiments disclosed herein are illustrative and non-restrictive in every respect. The scope of the present invention is defined by the terms of the claims and is intended to include any modifications within the meaning and scope equivalent to the terms of the claims.

What is claimed is:

1. A co-culture system comprising:
an anaerobic chamber having an internal space which is maintained in a first anaerobic environment; and
a co-culture apparatus disposed in the internal space of the anaerobic chamber, the co-culture apparatus comprising:
  a co-culture device, including
    a membrane having a first main surface, and a second main surface opposite to the first main surface, the second main surface configured for culturing cells in a second anaerobic environment,
    a first flow path partially defined by the first main surface, the first flow path disposed such that the first culture medium flows therethrough, and
    a second flow path partially defined by the second main surface, the second flow path disposed such that the second culture medium flows therethrough;
  a first airtight container accommodating a first culture medium source therein, the first airtight container having an interior space maintained in an aerobic environment;
  a second culture medium source for supplying a second culture medium to the co-culture device, the second culture medium source being disposed outside the first airtight container and exposed to the first anaerobic environment, which causes the second culture medium having to have a lower dissolved oxygen concentration than that of the first culture medium; and
  a first conduit fluidically connected to the first flow path of the co-culture device and the first culture medium source, the first conduit communicating with the interior space of the first airtight container in an airtight manner.

2. The co-culture system according to claim 1,
wherein the co-culture device is disposed outside of the first airtight container,
wherein the co-culture device includes a first plate-shaped member and a second plate-shaped member sandwiching the membrane from a side of the first main surface and a side of the second main surface, and
wherein the first conduit is connected to the first plate-shaped member.

3. The co-culture system according to claim 1,
wherein the co-culture device includes a culture tank having a bottom surface on which the membrane is disposed, and
wherein the first airtight container has an opening to receive the co-culture device.

4. The co-culture system according to claim 1,
wherein the co-culture apparatus further comprises a first drive source that supplies the first culture medium stored in the first culture medium source to the first flow path via the first conduit, and
wherein the first drive source is disposed in the first airtight container.

5. The co-culture system according to claim 1,
wherein the co-culture device has a first surface facing the first airtight container, and a second surface opposite to the first surface,
wherein the inlet of the first flow path is formed in the first surface, and
wherein an outlet of the first flow path, an inlet of the second flow path, and an outlet of the second flow path are formed in the second surface.

6. The co-culture system according to claim 1,
wherein the co-culture apparatus further comprises a second airtight container,
wherein the co-culture device is disposed in the second airtight container.

7. The co-culture system according to claim 6, wherein the co-culture apparatus further comprises:
a second conduit connecting an inlet of the second flow path and the second culture medium source; and
a second drive source that supplies the second culture medium stored in the second culture medium source to the second flow path via the second conduit, wherein the second drive source and the second culture medium source are disposed in the second airtight container.

8. A co-culture method comprising:
placing a co-culture apparatus in an anaerobic chamber having an internal space which is maintained in a first anaerobic environment,
the co-culture apparatus disposed in the internal space of the anaerobic chamber and including:
  a co-culture device, including
    a membrane having a first main surface, and a second main surface opposite to the first main surface, the second main surface configured for culturing cells in a second anaerobic environment,
    a first flow path partially defined by the first main surface, the first flow path disposed such that the first culture medium flows therethrough, and
    a second flow path partially defined by the second main surface, the second flow path disposed such that the second culture medium flows therethrough;

a first airtight container accommodating a first culture medium source therein, the first airtight container having an interior space maintained in an aerobic environment, a second culture medium source for supplying a second culture medium to the co-culture device, the second culture medium source being disposed outside the first airtight container and exposed to the first anaerobic environment, which causes the second culture medium to have a lower dissolved oxygen concentration than that of the first culture medium, and a first conduit fluidically connected to the first flow path of the co-culture device and the first culture medium source, the first conduit communicating with the interior space of the first airtight container in an airtight manner, supplying a first culture medium from the first culture medium source to the first flow path; and supplying a second culture medium from the second culture medium source to the second flow path, wherein the first culture medium supplied to the first flow path is maintained in the aerobic environment within the anaerobic chamber.

* * * * *